United States Patent [19]

Matsunaga et al.

[11] Patent Number: 5,180,871
[45] Date of Patent: Jan. 19, 1993

[54] PROCESS FOR PRODUCING PHENOLS

[75] Inventors: Fujihisa Matsunaga; Hiroshi Fukuhara; Mitsuki Yasuhara, all of Ichihara, Japan

[73] Assignee: Mitsui Petrochemical Industries, Ltd., Tokyo, Japan

[21] Appl. No.: 839,683

[22] Filed: Feb. 24, 1992

Related U.S. Application Data

[63] Continuation of Ser. No. 657,363, Feb. 19, 1991, abandoned, which is a continuation of Ser. No. 266,940, Nov. 3, 1988, abandoned.

[30] Foreign Application Priority Data

Nov. 11, 1987 [JP] Japan ............................... 62-285001

[51] Int. Cl.$^5$ ............................................. C07C 15/02
[52] U.S. Cl. ..................................... 585/400; 568/799
[58] Field of Search ......................... 568/799; 585/400

[56] References Cited

U.S. PATENT DOCUMENTS

| | | | |
|---|---|---|---|
| 2,321,551 | 6/1943 | Loder | 568/799 |
| 3,326,994 | 6/1967 | Matsen et al. | 260/668 |
| 3,580,970 | 11/1967 | Sweet | 568/799 |
| 3,859,465 | 1/1975 | Young | 568/799 |
| 4,083,883 | 4/1978 | Hayes | 208/139 |
| 4,366,091 | 12/1982 | Antos | 585/444 |
| 4,538,009 | 8/1985 | Goetz et al. | 568/799 |

FOREIGN PATENT DOCUMENTS

| | | | |
|---|---|---|---|
| 249739 | 4/1963 | Australia | 568/799 |
| 53-46938 | 4/1978 | Japan . | |
| 56-95127 | 8/1981 | Japan . | |
| 56-95130 | 8/1981 | Japan . | |
| 57-130926 | 8/1982 | Japan . | |
| 58-164524 | 9/1983 | Japan . | |
| 58-164525 | 9/1983 | Japan . | |
| 58-172323 | 10/1983 | Japan . | |
| 59-155328 | 9/1984 | Japan . | |
| 59-193836 | 11/1984 | Japan . | |
| 60-202829 | 10/1985 | Japan . | |
| 61-122231 | 6/1986 | Japan . | |
| 61-221141 | 10/1986 | Japan . | |
| 61-293939 | 12/1986 | Japan . | |
| 62-45544 | 2/1987 | Japan . | |
| 62-120333 | 6/1987 | Japan . | |
| 939613 | 10/1963 | United Kingdom | 568/799 |
| 1011432 | 12/1965 | United Kingdom | 568/799 |

OTHER PUBLICATIONS

The Journal of Organic Chemistry, vol. 34, No. 12, (1969) pp. 3949–3952.
J.C.S., Chem. Comm., (1981) pp. 1274–1275.
Acta Chimica Hungarica 122(2), (1986) pp. 175–180.

Primary Examiner—Olik Chaudhuri
Assistant Examiner—G. Fourson
Attorney, Agent, or Firm—Nixon & Vanderhye

[57] ABSTRACT

A process for producing a phenol from the steps of:
(a) partially hydrogenating a benzene, followed by separating the reaction mixture into respective components of a cyclohexene, a cyclohexane and a benzene;
(b) oxidizing or hydrating the separated a cyclohexene into oxygen-containing compounds of a cyclohexane;
(c) dehydrogenating the oxygen-containing compounds of a cyclohexane into a phenol;
(d) dehydrogenating the cyclohexane separated in step (a) to convert the cyclohexane into a benzene; and
(e) returning a part or all of hydrogen formed in steps (c) and (d) back to step (a).

8 Claims, No Drawings

PROCESS FOR PRODUCING PHENOLS

CROSS-REFERENCE TO RELATED APPLICATIONS

This application is a continuation of earlier application Ser. No. 07/657,363, filed Feb. 19, 1991, now abandoned, which is a continuation of Ser. No. 07/266,940, filed Nov. 3, 1988, now abandoned.

BACKGROUND OF THE INVENTION

1. Field of the Invention

The present invention relates to a process for producing a phenol from a benzene.

2. Description of the Related Art

Already known are a process for producing cyclohexenes by a partial hydrogenation of benzenes in the liquid phase, a process for producing oxygen-containing compounds of cyclohexenes such as cyclohexanones, cyclohexenones, and cyclohexenols by an oxidation of cyclohexenes with molecular oxygen, a process for producing cyclohexanols by a hydration of cyclohexenes, and a process for producing phenols by a dehydrogenation of cyclohexanones or cyclohexanols. Also known are a process for converting cyclohexanes into benzenes by dehydrogenation, and a process for separating benzenes, cyclohexenes, and cyclohexanes.

Processes for producing cyclohexenes by a partial hydrogenation of benzenes in the liquid phase are disclosed in, for example, Japanese Unexamined Patent Publications (Kokai) No. 48-36150, No. 53-46938, No. 57-130926, No. 59-155328, No. 60-184031, No. 60-202829, No. 61-122231 and No. 62-45544. According to the process of Japanese Unexamined Patent Publication (Kokai) No. 62-45544, for example, cyclohexenes can be obtained by a partial hydrogenation of benzenes in the presence of zinc sulfate by using a catalyst obtained by a reduction of Ru compounds containing Zn compounds with hydrogen.

Processes for producing oxygen-containing compounds by an oxidation of cyclohexenes with molecular oxygen are disclosed in, for example, J.O.C., Vol. 34, No. 12, P 3949–3952 (1969), J.C.S., Chem. Comm., P 1274–1275 (1981), and Acta Chimica Hungarica 122 (2), P 175–180 (1980). According to the process disclosed in Acta Chimica Hungarica 122 (2), p 175 (1986), for example, cyclohexanones can be obtained by an oxidation of cyclohexenes with molecular oxygen by using copper ketenide ($Cu_2C_2O$) as the catalyst.

Processes for producing cyclohexanols by a hydration of cyclohexenes are disclosed in Japanese Patent Publications (Kokoku) No. 38-15619, No. 43-8104, Japanese Unexamined Patent Publications (Kokai) No. 59-193836, No. 61-293939, Journal of Petroleum Society of Japan, 28 (2), P 172-5, Japanese Unexamined Patent Publications (Kokai) No. 61-221141 and No. 62-120333. According to the process of Japanese Unexamined Patent Publication (Kokai) No. 61-293939, for example, cyclohexanols can be produced by a hydration of cyclohexenes in the liquid phase in the presence of a molybdenum compound, by using p-toluenesulfonic acid as the catalyst.

A process for producing phenols by a dehydrogenation of cyclohexanones or cyclohexanols is disclosed in, for example, Japanese Patent Publication (Kokoku) No. 44-6810. According to this process, phenols can be produced by a dehydrogenation of cyclohexanones or cyclohexanols under gas phase reaction conditions by using a platinum compound as the catalyst.

Processes for producing benzenes from cyclohexanes are widely known, as disclosed in, for example, U.S. Pat. No. 3,326,994, U.S. Pat. No. 4,366,091, U.S. Pat. No. 4,083,883. According to the process of U.S. Pat. No. 4,083,883, benzenes can be produced by a dehydrogenation of cyclohexanes under gas phase reaction conditions by using a catalyst comprising a combination of platinum, rhodium, and nickel carried on alumina.

Processes for separating benzenes, cyclohexenes, and cyclohexanes are disclosed in, for example, Japanese Unexamined Patent Publications (Kokai) No. 51-127043, No. 58-172323, No. 56-95130, No. 56-95127, No. 58-164524, and No. 58-164525. According to the process of Japanese Unexamined Patent Publication (Kokai) No. 51-127043, for example, the respective components can be separated with a good yield by an extraction distillation, using dimethyl sulfoxide as the solvent.

As described above, processes for the production of cyclohexenes, processes for the production of cyclohexanones, cyclohexenones, and cyclohexanols, and processes for the production of phenols by a dehydrogenation of cyclohexanones or cyclohexanols are known, but a process for the production of phenols from benzenes by using hydrogen as a mediating agent is not known.

SUMMARY OF THE INVENTION

Accordingly, the objects of the present invention are to eliminate the above-mentioned disadvantages of the prior art and to provide a process for producing a phenol from a benzene, by using hydrogen as a mediating agent, by combining the reduction reaction and the oxidation reaction wherein oxygen-containing compounds such as a cyclohexanone, a cyclohexenone, a cyclohexanol or a cyclohexenol, and hydrogen formed by a dehydrogenation of a cyclohexane and the oxygen-containing compounds can be utilized to effect the hydrogenation reaction of a benzene with forming no substantial amount, or an only slight amount, of hydrogen as a by-product.

Other objects and advantages of the present invention will be apparent from the following description.

In accordance with the present invention, there is provided a process for producing a phenol, comprising the steps of:

(a) partially hydrogenating a benzene, followed by separating the reaction mixture into respective components of a cyclohexene, a cyclohexane, and a benzene;

(b) oxidizing or hydrating the separated cyclohexene into oxygen-containing compounds of a cyclohexane;

(c) dehydrogenating the above oxygen-containing compounds of a cyclohexane into a phenol;

(d) dehydrogenating the cyclohexane separated in step (a) to convert the cyclohexane into a benzene; and (e) returning at least a part of the hydrogens formed in steps (c) and (d) to step (a).

DESCRIPTION OF THE PREFERRED EMBODIMENTS

In the present invention, a benzene or benzenes, a phenol or phenols, a cyclohexane or cyclohexanes, a cyclohexene or cyclohexene, a cyclohexanone or cyclohexanones, a cyclohexanol or cyclohexanols, and a cyclohexenol or cyclohexenols include, in addition to benzene, phenol, cyclohexane, cyclohexene, cyclohexanone, cyclohexanol, and cyclohexenol, other derivatives thereof substituted with substituents such as hydrocarbon groups (e.g., $C_1$-$C_4$ alkyl group) or halogen atoms (e.g., Br and Cl).

In the present invention, in step (a), cyclohexenes are produced by a partial hydrogenation of benzenes in the liquid phase, and the reaction in this case can be carried out by, for example, the following method. Namely, a mixture of benzenes and water is charged together with a hydrogenation catalyst and an additive for accelerating the reaction into an autoclave, and a hydrogenation reaction is caused by stirring and vigorously mixing the contents in the autoclave under a predetermined pressure. As the hydrogenation catalyst in this case, a ruthenium-zinc alloy prepared from a mixture of ruthenium chloride and zinc chloride can be exemplified. As the additive for accelerating the reaction, zinc compounds such as zinc sulfate and zinc phosphate can be exemplified. The amount of the catalyst used is 0.05 to 10% by weight based on the benzenes. The amount of the additive is 0.1 to 30% by weight, preferably 0.5 to 10% by weight, as the concentration in water. The reaction is carried out at a temperature of from 50° to 250° C., preferably 100 to 200° C. The reaction pressure is from 5 to 150 kgf/cm², preferably 10 to 100 kgf/cm².

In the partial hydrogenation reaction, a reaction mixture containing unreacted benzenes and by-products of cyclohexanes is obtained, and the respective components of cyclohexenes, cyclohexanes and benzenes are separated as the starting material for the next step. In this case, the cyclohexenes, cyclohexanes and benzenes can be separated by a multi-stage extraction distillation using a specific solvent. More specifically, when an extraction distillation is performed by feeding a mixture of cyclohexenes, cyclohexanes, and benzenes into the intermediate stage of the extraction distillation tower in the first stage, while feeding dimethyl sulfoxide as the solvent to the tower top, cyclohexanes are distilled out from the tower top. The mixture of cyclohexenes, benzenes and dimethyl sulfoxide withdrawn from the first tower bottom is fed to the second distillation tower (intermediate stage) to distill out cyclohexenes from the tower top, and the mixture withdrawn from the second tower bottom is delivered to the third distillation tower, wherein benzenes are separated from dimethyl sulfoxide.

The cyclohexenes thus obtained are delivered to the next step (b) for oxidation or hydration, the cyclohexanes are delivered to a later step (e) to be returned to benzenes by dehydrogenation, and the benzenes are returned to the previous step (a).

In step (b) of the present invention, cyclohexenes are oxidized with molecular oxygen to be converted to oxygen-containing compounds of cyclohexanes such as cyclohexanones, cyclohexenones, and cyclohexenols, or cyclohexenes are hydrated to produce oxygen-containing compounds of cyclohexane comprising cyclohexanols. The following method of oxidizing cyclohexenes with molecular oxygen, for example, can be employed. Namely, cyclohexenes and a solvent are charged together with a catalyst into an autoclave, and oxidized by blowing oxygen or air while vigorously stirring the contents. In this case, a solvent may be employed, if desired, and preferable solvents include polar solvents such as alcohols. Examples of the catalyst include copper ketenide, palladium sulfate, and palladium chloride. The amount of catalyst used may be 0.1 to 10% by weight, preferably 0.3 to 5% by weight, as the concentration in the reaction mixture. The reaction temperature may be from room temperature to 150° C., and the pressure may be either normal pressure or a predetermined higher pressure, provided that the reaction mixture can be maintained in the liquid phase.

The following method can be employed for producing cyclohexanols by a hydration of cyclohexenes. Namely, cyclohexenes and water are charged together with a catalyst into an autoclave, and the reaction is carried out under heating while vigorously stirring the reaction mixture. As the catalyst, an alkylbenzenesulfonic acid such as p-toluenesulfonic acid or a sulfonic acid type ion exchange resin, may be employed. The amount of catalyst employed may be 10 to 70% by weight based on the reaction mixture. In this case, an additive for accelerating the reaction, for example, a molybdenum compound or a vanadium compound, may be added. The amount of the additive may be 0.01 to 5% by weight based on the catalyst. The reaction temperature is from 50 to 200° C., preferably from 90 to 150° C. The pressure may be a normal pressure or a higher pressure, provided that the reaction mixture is maintained in the liquid phase.

In step (c) of the present invention, oxygen-containing compounds of cyclohexanes such as cyclohexanones, cyclohexenones, and cyclohexanols obtained by an oxidation of cyclohexenes, or cyclohexanols obtained by a hydration of cyclohexenes, are dehydrogenated to produce phenols. The following method can be employed in this case. Namely, the above oxygen-containing compounds obtained from cyclohexenes are subjected to a dehydrogenation reaction under gas phase reaction conditions in the presence of a catalyst. As the catalyst, a platinum-potassium carbonate system catalyst carried on silica is used. The reaction temperature may be from 300° to 500° C. The amount of the reaction mixture fed into the catalyst may be 0.01 to 10 Hr$^{-1}$, preferably 0.05 to 3 Hr$^{-1}$, in terms of LHSV.

Of the above oxygen-containing compounds obtained by an oxidation of cyclohexenes, in the dehydrogenation reaction of cyclohexenols, the yield of phenols is lowered because of the formation of benzenes as a side reaction. Accordingly, in the oxidation of cyclohexenes, when a reaction mixture containing a large amount of cyclohexenols is obtained, preferably the cyclohexanols are converted to cyclohexanones by the method described below before subjecting the mixture to the dehydrogenation reaction. Namely, when a heat treatment is effected with the addition of a catalyst to the reaction mixture containing cyclohexanols, the cyclohexanols are converted to cyclohexanones. In this case, dichlorotrisphenylphosphine ruthenium may be used as the catalyst and the reaction temperature may be 150° to 220° C. The reaction pressure may be sufficient to maintain the reaction mixture in the liquid phase. Accordingly, a dehydrogenation reaction is carried out after the conversion of cyclohexanols to cyclohexanones, whereby a lowered yield due to a by-production of benzenes can be prevented.

Cyclohexanes by-produced in the partial hydrogenation step of benzenes in step (a) are purified by separation in the extraction distillation step, and then subjected to a dehydrogenation reaction to be converted to benzenes. In this case, the following reaction can be employed. Namely, when a catalyst having a platinum group metal carried on a porous carrier is used, cyclohexanes are permitted to pass under gas phase reaction conditions to be converted to benzenes. As the platinum group metal, there may be included platinum, palladium, rhodium, and ruthenium or the like. The catalyst is prepared by combining two or more kinds thereof, and adding nickel or the like thereto. As the porous carrier for carrying the metal thereon, refractory inorganic oxides such as alumina, titania, and zirconia, may be employed, although preferably alumina is used. The reaction temperature may be within 370° to 650° C., and the pressure within 0.1 to 10 atm. The LSHV may be 1 to 40 $Hr^{-1}$, and the molar ratio of hydrogen to hydrocarbon may be preferably from 1:1 to 20:1.

In the present invention, since hydrogen gas is generated at the step (c) when producing phenols from oxygen-containing compounds of cyclohexanes and at step (d) when converting cyclohexanes to benzenes, the gas discharged from the reaction is fed to a condenser to remove liquid components therein other than hydrogen gas, compressed in a compressor, and returned to step (a) for the production of cyclohexenes by a partial hydrogenation of benzenes.

In the present invention, the hydrogen gas necessary as the reaction starting material when producing cyclohexenes from benzenes, a part or all thereof, is byproduced from the step of producing phenols from oxygen-containing compounds of cyclohexanes as described above, and the step of converting cyclohexanes to benzenes.

In the present invention, the quantitative ratio ((B+C)/A molar ratio) of the amount (A) of hydrogen gas used for the reaction used in step (a) when producing cyclohexenes from benzenes, the amount (B) of hydrogen gas generated in step (c) when producing phenols from oxygen-containing compounds of cyclohexanes, and the amount (C) of hydrogen gas generated in step (d) when converting cyclohexanes to benzenes is within 1.0 to 2.0, and thus hydrogen gas generated in steps (c) and (d) can be effectively and economically utilized. Therefore, a practical and economical process for producing phenols from benzenes can be provided according to the process of the present invention.

Effect of the Invention

According to the process of the present invention, by combining the respective steps (a) to (e) as described above in the method of producing phenols from benzenes as the starting material, phenols can be produced from benzenes, and hydrogen gas generated during the production of phenols from oxygen-containing compounds of cyclohexanes obtained from the cyclohexenes, and hydrogen gas generated when converting cyclohexanes to benzenes, can be effectively utilized for the production of cyclohexenes by a partial hydrogenation of benzenes, whereby the economy of the process as a whole can be remarkably enhanced. Particularly, according to the process of the present invention, the amount of hydrogen gas required for a partial hydrogenation of benzenes becomes substantially equal to the amount of hydrogen gas generated in the dehydrogenation step of oxygen-containing compounds of cyclohexanes and the amount of hydrogen gas generated when converting cyclohexanes to benzenes, and therefore, phenols are produced from benzenes with hydrogen as the mediating agent, to effect an efficient production.

EXAMPLES

The present invention will now be further illustrated by, but is by no means limited to, the following Examples.

EXAMPLE 1

Production of Cyclohexene

Into an 0.5-liter autoclave made of titanium were charged 0.2 g of a ruthenium-zinc alloy catalyst obtained by reducing $Ru(OH)_3$ containing $Zn(OH)_2$, 40 g of benzene and 160 g of water. After the autoclave was internally replaced with nitrogen, the temperature was elevated while stirring the contents. When the temperature in the autoclave reached 150° C., hydrogen was pressurized to 50 $kgf/cm^2$ and the reaction was carried out for 120 minutes. Since the pressure was lowered by a consumption of hydrogen during the reaction, the hydrogen was periodically supplemented. After the autoclave was cooled, the reaction mixture was taken out and the oil phase was separated from the aqueous phase, to give 40.9 g of the oil phase. As a result of an analysis of the obtained oil phase, the conversion of benzene was found to be 40.3% and the cyclohexene yield was 30.2% (selectivity 74.9%). As other products, cyclohexane was obtained at a yield of 10.1%.

Separation of Cyclohexane, Cyclohexene, and Benzene

Separation was conducted by an extraction distillation using a 50-stage distillation tower equipped with a feeding inlet at the intermediate stage. To the 20th stage, counted from the tower top, 100 parts of the above reaction mixture were continuously fed, while 500 parts of dimethyl sulfoxide were continuously fed to the tower top, to carry out a continuous distillation under normal pressure. Under a reflux ratio of 18, 10 parts of cyclohexane with a purity of 95% were obtained as the tower top distillate, and 590 parts of a mixture of cyclohexene, benzene, and dimethylsulfoxide were obtained from the tower bottom.

The mixture was again subjected to extraction distillation, to separate other components. By using the distillation tower used above, the above mixture was continuously fed to the 25th stage, counted from the tower top, and a continuous distillation was carried out under a reflux ratio of 12, and 30 parts of cyclohexene (purity 95%) were obtained from the tower top. The mixture of benzene and dimethyl sulfoxide discharged from the tower bottom was subjected to batchwise distillation by using a 10-stage distillation tower to separate the benzene.

The respective components thus separated were delivered to the next step, and dimethylsulfoxide was used again as the starting material for the extraction distillation.

Oxidation of Cyclohexene

The cyclohexene distillate (32.8 g) obtained by the above extraction distillation and 0.43 g of a catalyst (copper ketenide) were charged into an 100 ml autoclave of SUS-316, and air was blown at a rate of 20 liters/hr while stirring of the contents, under a reaction temperature of 40° C. and a pressure of 10 $kgf/cm^2$, to carry out the reaction for 6 hours. After completion of the reaction, the reaction mixture was taken out and the catalyst filtered off to obtain 37.3 g of the reaction mixture. As a result of an analysis of the reaction mixture, 49.5% of cyclohexene contained in the starting oil phase was found to have reacted and cyclohexanone was formed at a selectivity of 90%.

Production of Phenol

A stainless steel cylindrical gas phase reactor having an inner diameter of 2.5 cm was filled with 20 ml of a particulate solid catalyst having 1% of platinum and 0.5% of potassium carbonate carried thereon. While the reactor was heated to 400° C., hydrogen was permitted to flow at a flow rate of 50-liters/hr for 8 hours to activate the catalyst. Under a reaction temperature of 400° C. and a normal pressure, the reaction mixture obtained by the above oxidation reaction was fed at a flow rate of 10 ml/hr, and at the same time, hydrogen was fed at a flow rate of 1.5 liters/hr to maintain the activity of the catalyst. The reaction mixtures discharged from the bottom of the reactor were collected and the composition thereof analyzed. As a result, 99.6% of cyclohexanone contained in the starting material fed was found to have reacted and phenol was formed at a selectivity of 96.0%. On the other hand, hydrogen was discharged at 3.1 liters/hr from the reactor outlet, and was recovered and provided as the reaction starting material for a partial hydrogenation of benzene.

Conversion of Cyclohexane to Benzene

Cyclohexane separated by an extraction distillation of the reaction mixture in the benzene partial hydrogenation step was subjected to a dehydrogenation reaction as described below.

A catalyst having 0.3 wt.% of platinum, 0.1 wt.% of rhodium and 0.2 wt.% of alumina carried thereon (chlorine content of 0.2% or less) was filled into a reaction tube, and a dehydrogenation reaction was carried out under a reaction temperature of 480° C., a pressure of 7 kgf/cm$^2$, and an LHSV of 3.0 Hr$^{-1}$. The product gas mixture discharged from the outlet of the reaction tube was circulated as a recycling gas to the reaction tube inlet, and cyclohexane was fed at a ratio of ¼ mole relative to the recycling gas. When the reaction system was stabilized, the reaction product was analyzed and it was found that cyclohexane was substantially quantitatively converted to benzene. The benzene and hydrogen obtained in this reaction were returned to the previous step.

EXAMPLE 2

A partial hydrogenation of benzene and a production of cyclohexene by extraction distillation were conducted in the same manner as described in Example 1.

Hydration of Cyclohexene

The cyclohexene distillate (65 g) separated by extraction distillation, 120 g of 67% p-toluenesulfonic acid, and 0.8 g of molybdenum trioxide were charged into a 0.5-liter autoclave made of titanium, and the autoclave was pressurized to an initial pressure of 5 kgf/cm$^2$. After a reaction at 120° C. for one hour, the autoclave was cooled and the contents were taken out, the reaction mixture was separated into an aqueous phase and an oil phase, and the respective phases were quantitatively analyzed for cyclohexene and cyclohexanol. As a result, 55.7% of cyclohexene contained in the starting material was found to have reacted, and 92.6% of reacted cyclohexene was converted to cyclohexanol.

The hydrated reaction mixture was distilled under a normal pressure by using a 10-stage distillation column, and 27.2 g of cyclohexene and 31.8 g of cyclohexanol were separated. The cyclohexene was delivered to the hydration step and the cyclohexanol to the dehydrogenation step.

Production of Phenol

The cyclohexanol obtained by a distillation separation of the above hydrated reaction mixture was provided for the dehydrogenation reaction according to the method of Example 1, and as a result, 95.5% of the cyclohexanol fed was found to have reacted, and 88.8% of the cyclohexanol was converted to phenol. As other by-products, benzene was obtained at a selectivity of 8.0% and cyclohexanone at a selectivity of 2.9%. Hydrogen obtained during the dehydrogenation reaction and benzene cyclohexanone of the above-mentioned by-products were all returned to each previous step.

In the above Examples 1 and 2, the quantitative ratio of ((B+C)/A molar ratio) of the amount of hydrogen gas (A) used for the reaction in step (a) when producing cyclohexene from benzene, the amount of hydrogen gas (B) generated in step (c) when producing phenol from oxygen-containing compounds of cyclohexane, and the amount of the hydrogen gas (C) generated in step (d) when converting cyclohexane to benzene, is within 1.0 to 20, whereby phenol can be produced with the generated hydrogen gas.

We claim:

1. A process for producing a phenol compound selected from the group consisting of phenol and derivatives thereof substituted with at least one substituent selected from the group consisting of an $C_1$-$C_4$ alkyl group and a halogen atom said process comprising the steps of:
    (a) partially hydrogenating a benzene compound selected from the group consisting of benzene and derivatives thereof substituted with at least one substituent selected from the group consisting of $C_1$-$C_4$ alkyl groups and halogen atoms, followed by separating the reaction mixture into the respective components of the resultant cyclohexene and cyclohexane compounds and the unreacted benzene compound;
    (b) oxidizing ör hydrating the separated cyclohexene compound into the corresponding oxygen-containing compound selected from eh group consisting of the corresponding cyclohexanone compound, cyclohexenone compound, cyclohexanol compound and cyclohexenol compound;
    (c) dehydrogenating the oxygen-containing compound into the corresponding phenol compound;
    (d) dehydrogenating the cyclohexane compound separated in step (a) to form the benzene compound;
    (e) returning at least a part of hydrogen formed in dehydrogenation steps (c) and (d) to step (a).

2. The process as claimed in claim 1, wherein the partial hydrogenation in step (a) is conducted in the liquid phase.

3. The process as claimed in claim 1, wherein step (b) comprises oxidizing the cyclohexene compound with molecular oxygen to the corresponding oxygen-containing compound.

4. The process of claim 1 wherein step (b) comprises hydrating th cyclohexene compound into the cyclohexanol compound.

5. The process as claimed in claim 1, wherein the step (c) the oxygen-containing compound is a cyclohexenol compound which is converted into the cyclohexanone compound, followed by dehydrogenating the cyclohexanone compound.

6. A process for producing a phenol compound selected from the group consisting of phenol and derivatives thereof substituted with at least one substituted selected from the group consisting of a $C_1$-$C_4$ alkyl group and a halogen atom said process comprising the steps of:

(a) partially hydrogenating a benzene compound selected from the group consisting of benzene and derivatives thereof substituted with at least one substituent selected from the group consisting of $C_1$-$C_4$ alkyl groups and halogen atoms, followed by separating the reaction mixture into the respective components of the resultant cyclohexane and cyclohexane compounds and th unreacted benzene compound;

(b) hydrating the separated cyclohexene compounds into the corresponding oxygen-containing compound;

(c) dehydrogenating the oxygen-containing compound into the corresponding phenol compound;

(d) dehydrogenating the cyclohexane compound separated in step (a) to from the benzene compound;

(e) returning at least a pat of hydrogen formed in dehydrogenation steps (c) and (d) to step (a).

7. The process as claimed in claim 6, wherein the partial hydrogenation in step (a) is conducted in the liquid phase.

8. The process as claimed in claim 6, wherein in step (c) the oxygen-containing compound is a cyclohexenol compound which is converted into a cyclohexanone compound, followed by dehydrogenating the cyclohexanone compound.

* * * * *